United States Patent [19]

Grice et al.

[11] Patent Number: 4,939,301

[45] Date of Patent: Jul. 3, 1990

[54] PRODUCTION OF ETHANOLAMINE BY AMINATION OF ETHYLENE OXIDE OVER ACID ACTIVATED CLAYS

[75] Inventors: Neal J. Grice; John F. Knifton, both of Austin, Tex.

[73] Assignee: Texaco Chemical Company, White Plains, N.Y.

[21] Appl. No.: 289,105

[22] Filed: Dec. 23, 1988

[51] Int. Cl.$^5$ ............................................. C07C 89/02
[52] U.S. Cl. .................................... 564/477; 564/475; 564/478; 564/479; 502/81
[58] Field of Search ............... 564/477, 478, 475, 479; 502/81

[56] References Cited

U.S. PATENT DOCUMENTS 4,329,257  5/1982  Sommer et al. ...................... 502/81
4,438,281  3/1984  Johnson, Jr. ......................... 564/477

Primary Examiner—Richard L. Raymond
Assistant Examiner—Brian G. Bembenick
Attorney, Agent, or Firm—Jack H. Park; Kenneth R. Priem; Cynthia L. Kendrick

[57] ABSTRACT

A process for preparing monoalkanolamines from ammonia and alkylene oxide using a catalyst which allows for high selectivity and high productivity which comprises an acid modified montmorillonite clay.

13 Claims, No Drawings

PRODUCTION OF ETHANOLAMINE BY AMINATION OF ETHYLENE OXIDE OVER ACID ACTIVATED CLAYS

BACKGROUND OF THE INVENTION

1. Field of the Invention

The invention relates to a process for the preparation of monoethanolamines by amination of ethylene oxide with ammonia using acid activated clay catalysts. These clays which have been treated with acid have particular properties which provide greatly enhanced reactor productivity while maintaining very high selectivity for monoethanolamine.

2. Description of the Related Art

Most of the efforts regarding the production of monoalkanolamines have been concerned with the manufacture of monoethanolamine (MEA) from the reaction of ammonia with ethylene oxide.

*The Kirk-Othmer Encyclopedia of Chemical Technology*, Third Edition describes the standard manufacture of MEA from the reaction of ethylene oxide with an excess of aqueous ammonia at a temperature of about 50° to 100° C., see Vol. 1, pp. 95–952 and Vol. 9, p. 437.

It was accepted for a long time, and originally demonstrated by Knorr in 1987, that a small proportion of water was essential to such a reaction since pure ethylene oxide does not react with anhydrous ammonia (Bev., 1987, Vol. 30, p. 909 and 1899, Vol. 32, p. 729). For a background on this reaction, showing a general acceptance that the presence of water was required, see Ellis, Carleton, *The Chemistry of Petroleum Derivatives*, New York: Reinhold, Vol. 1, pp. 541–544 (1934) and Vol. 2, pp. 563, 567 (1937) and Miller, S. A., *Ethylene and Its Industrial Derivatives*, London: Ernest Benn Limited, pp. 16–17; 22,632–635 (1969).

Acids have been used as catalysts or cocatalysts in a number of reactions described. U.S. Pat. No. 2,186,392 reveals that ethanolamines may be produced from ammonia or a primary amine and ethylene oxide and a salt of a weak acid, such as ammonium carbonate, in the presence of an aliphatic radical which is positive with respect to hydrogen. See Chemical Abstracts (CA) 36:4131-2. Tertiary amines with hydroxyalkyl radicals may be made from ammonia, primary or secondary amines and an alkylene oxide at a temperature of from 30° to 60° C., with improved yields being possible if water or a weak acid is also present. See German Patent No. 844,449 (CA 48:1429c). British Patent No. 497,093 teaches that monoalkanolamines may be made from olefin oxides and ammonia in the presence of water and an acid (see CA 36:4131-8).

Another catalyst which has been the object of research is aluminum oxide. M. Sile, et al in two articles titled "Catalyst Reaction of Ethylene Oxide with Ammonia", found that ethylene oxide and ammonia may be reacted together at high temperatures (350°–700° C.) over aluminum oxide, phosphate catalysts and 13X zeolites to yield a large number of products of which ethanolamines were only a small part, including pyridine, alpha- and gamma-picolines, acetic acid, piperazine, aziridine, diethylamine, ethylenediamine and dioxane, see Latv. PSR Zinat, Akad, Vestis, Kim. Serv., Vol. 1972, parts 1 and 2, pp. 54–60 and 218–23, respectively, (CA 77:5243f and 88175j). More specifically, aluminum oxide at 350° to 450° gives pyridine, alpha- and gamma-picolines, acetic acid, alpha-aminoethanol and dioxane; zeolite 13X at 388° to 450° gave instead pyridine, alpha- and gamma-picolines, dioxane, piperazine and a little ethylenimine, diethylamine and ethylenediamine while different phosphates gave pyridine, alpha- and gamma-picolines, acetic acid, alpha-aminoethanol and ethylenimine.

In other work it is taught that ethylene oxide and ammonia may be reacted together over aluminum oxide at 300° to 350° C. to produce ethanolamines and an aldehyde. See M. S. Malinonskii, *J. Applied Chem.* (USSR), Vol. 20, pp. 630–634 (1947).

U.S. Pat. No. 3,697,598 reveals a method by which monoalkanolamines may be made from excess ammonia and alkylene oxide without water in the presence of a cationic ion exchange resin at a temperature of at least 80° to 150° C. In Swedish Patent No. 158,167 to the same inventor, and referred to within the '598 patent, there is disclosed the reaction of alkylene oxides and ammonia in an anhydrous reaction system using as a catalyst organic and inorganic acids, ammonium salts and ion exchange resins. The advantage of such an anhydrous reaction is elimination of the water removal step. There is usually not as much stability at high temperatures with ion exchange resin catalysts as would be desirable. In addition, in some processes the selectivity to monoalkanolamines in proportion to di- and trialkanolamines is not as high as would be desirable.

In an article titled "Comparison of Some Solid Catalysts for the Production of Ethanolamines from Ammonia and Ethylene Oxide in the Liquid Phase", by L. Vamling and L. Cider in *Ind. Eng. Chem. Res. Dev.* 1986 (25) 424, there is a discussion of the ability of different forms of zeolites to catalyze the formation of mono- di-, and triethanolamines from ethylene oxide and ammonia in the liquid phase, as well as a comparison of zeolite catalysts with organic ion-exchange resins.

U.S. Pat. No. 4,438,281 discloses a method for selective production of monoalkanolamines from alkylene oxides and ammonia over acidic inorganic catalysts. Here the highest selectivity to monoethanolamine was 87%. The catalyst productivity was not as great as would be desirable, generally it is in the range of ca. 0.02–0.07 g MEA/cc/hr.

In an article titled "Catalysis: Selective Developments", *Chem. Systems Report* 84-3, 239–249, at Section 3.4320, the unusual properties of smectite clays which make them generally of interest as catalysts are discussed. These compositions are layered and exhibit a 2:1 relationship between tetrahedral and octahedral sites. In addition, the combination of cation exchange, intercalation and the fact that the distance between layers can be adjusted provide interesting possibilities.

There is a discussion of clay mineral catalysts, including "acid" montmorillonite clay catalysts in "Progress In Inorganic Chemistry", Vol. 35, p. 41 (1987). The process of pillaring this type of catalyst is discussed. The process of pillaring can convert a clay lamellar solid into a more heat resistant two dimensional zeolite material.

It would be a great advantage if a catalyst could be provided for production of monoalkanolamines which worked at very high space velocities and yet afforded high selectivities and yields with a smaller percentage of by-products. In addition it would be an advantage if the catalyst were stable at higher temperatures.

SUMMARY OF THE INVENTION

This invention concerns a process for preparing monoalkanolamines which comprises reacting an alkylene oxide with an excess of ammonia in a substantially anhydrous media, but in the presence of an acid activated clay catalyst wherein the surface of the clay has been modified to form acidic sites, said acid activated clays allowing for improvements in reactor productivity while maintaining high selectivity.

DETAILED DESCRIPTION OF THE PREFERRED EMBODIMENT

A process is provided for selectively producing monoalkanolamines, especially monoethanolamine, from ammonia and ethylene oxide using acid activated clay catalysts. The process is very attractive economically because high reactor productivity rates are obtained with this catalyst. The catalyst also exhibits high selectivity for monoethanolamines over di- or triethanolamines.

The process of the invention is applicable to any alkylene oxide having from 2 to 4 carbon atoms including ethylene oxide, propylene oxide, 1,2-butylene oxide, 2,3-butylene oxide and isobutylene oxide. The major product is therefore the corresponding monoalkanolamine, such as monoethanolamine, monopropanolamine and monobutanolamine (Eq. 1, where $R_1$, $R_2$, $R_3$ and $R_4$ are methyl, ethyl or hydrogen). Di and trialkanolamines

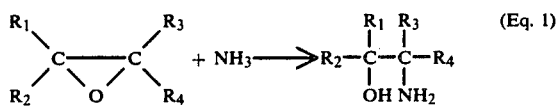
(Eq. 1)

may also be produced in small yields and they may be removed if desired. In this case however the advantages of the process relate to the unusually high selectivity to monoethanolamine (MEA).

Ammonia is the essential coreactant, but it should be present in anhydrous form to prevent the need to remove the water in the reactant stream. Alternatively, a lower alkyl primary or secondary amine containing 1-20 carbon atoms, such as methylamine, ethanolamine, iso-propylamine and n-hexylamine, can be used as the source of nitrogen in the reaction.

As discussed, the group of catalysts which works well in this synthesis is acid activated clay catalysts. Chemically clays are composed primarily of silicon, aluminum and oxygen with minor amounts of magnesium and iron in some cases. Variations in the ratios of these constituents, and their crystal lattice configurations, result in some fifty separate clays, each with its own characteristic properties.

Particularly effective in the reaction are smectite clays. Smectite clays are discussed in the article cited in Chem. Systems Report, 84-3. These clays have small particle size and unusual intercalation properties which afford them high surface area. They are alumino silicates with a unique structure that permits modifications which provide useful catalysts. They comprise layered sheets of octahedral sites between sheets of tetrahedral sites, and the distance between the layers can be adjusted by swelling, through treatment with the appropriate solvent, or treatment with a pillaring or Lewis acid reagent etc. What renders the smectites of particular interest among the clay minerals is their combination of cation exchange, intercalation and swelling properties.

The three-layer sheet types of smectite clays include montmorillonite, vermiculite and certain micas, all of which may be expanded between their layers by the appropriate treatment. The idealized basic structure of clays of this type is that of a pyrophyllite which has the basic formula $Si_8Al_4O_{20}(OH)_4$.

A general representation of the montmorillonite structure is:

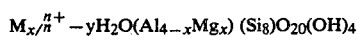

where M represents the interlamellar (balancing cation, normally sodium or lithium and x, y and n are integers.

These montmorillonite clays are best used in the present application and exhibit desirable properties when treated with acid. Acids activate montmorillonites by attacking and solubilizing structural cations in the octahedral layers. This opens up the clay structure and increases surface area. These acid treated clays act as strong Bronsted acids.

Acid activated montmorillonite clays are the preferred form of smectite clay in the present invention. Preferably these clays should have acidities in the range of 3 to 15, or greater, mg KOH/gm, titrated to a phenolphthalein end point. Their surface area should be $>30$ m$^2$/g, and preferably 200 to 1000 m$^2$/g. Their moisture content should be limited also, thereby upon heating to 220° F., the weight loss is generally less than 20 wt %.

Illustrative examples of suitable montmorillonite clays include powdered clays such Filtrol Grade 13, 113 and 160, sold by Harshaw-Filtrol, clays in granular form, such as Filtrol grade 24, having a 20-60 mesh size, and grade 25 (10/20 mesh) sold by Harshaw-Filtrol, as well as extruded clays such as the Filtrol Clay-62, sold in 1/16" and 3/16" diameter extrudates.

The performance of said montmorillonite clays in the subject synthesis of monoalkanolamines from alkylene oxides plus ammonia (Eq. 1) may be further enhanced by additional modification of the structure of said acidic clays. In particular it has been unexpectedly discovered that modification of the montmorillonite clays with heterpoly acids improves the performance of said clays by bringing about improvements both in terms of productivity and monoalkanolamines selectivity.

The heteropoly acids that are useful in the subject reaction comprise a class of acids formed by the condensation of two or more inorganic oxyacids. For example, phosphate and tungstate ions, when reacted in an acidic medium, are condensed to form 12-tungstophosphoric acid, a typical heteropoly acid (HPA) according to Equation 2:

A wide variety of elements ranging from Group I to Group VIII can become the central atom of the HPA anion, or the heteroatom as it is called (P in the case of Eq. 2). The nature of the heteroatom is a governing factor which determines both the condensation structure and the physical properties of the HPA.

Atoms coordinated to the heteroatom via oxygens are called polyatoms (W in the case of Equation 2) and in most cases are any one of such limited species as molybdenum, tungsten, niobium and vanadium. In the case of molybdenum (Mo) as the polyatom, the nature of the heteratoms, condensation ratios and chemical formulae of the corresponding HPA anions are summarized in Table I.

Anions containing the so-called Keggin structure have a condensation ratio of 1:12 and are the most typical of all HPA anions. Heteropoly acids with the Keggin structure, and their homologues, are generally the most readily available HPA's and the ones most commonly used in catalysis. The synthesis of these HPA's is well documented in the literature [see for example U.S. Pat. No. 3,947,332 (1976)].

TABLE 1

Typical heteropolymolybdate anions

| CONDENSATION RATIOS | | HETERO ATOMS (X) | CHEMICAL FORMULAS |
|---|---|---|---|
| 1:12 | Keggin structure | $P^{5+}$, $As^{5+}$, $Si^{4+}$, $Ge^{4+}$ | $[X^{n+}Mo_{12}O_{40}]^{-(8-n)}$ |
| | Silverton structure | $Ce^{4+}$, $Th^{4+}$ | $[X^{4+}Mo_{12}O_{42}]^{8-}$ |
| 1:11 | Keggin structure (decomposition) | $P^{5+}$, $As^{5+}$, $Ge^{4+}$, $Si^{4+}$ | $[X^{n+}Mo_{11}O_{39}]^{-(12-n)}$ |
| 2:18 | Dawson structure | $P^{5+}$, $As^{5+}$ | $[X_2^{5+}Mo_{18}O_{62}]^{6-}$ |
| 1:9 | Waugh structure | $Mn^{4+}$, $Ni^{4+}$ | $[X^{4+}Mo_9O_{32}]^{6-}$ |
| 1:6 | Anderson structure | | |
| | (A type) | $Te^{6+}$, $I^{7+}$ | $[X^{n+}Mo_6O_{24}]^{-(12-n)}$ |
| | (B type) | $Co^{3+}$, $Al^{3+}$, $Cr^{3+}$ | $[X^{n+}Mo_6O_{24}H_6]^{-(6-n)}$ |
| 4:12 | | $As^{5+}$ | $[H_4As_4Mo_{12}O_{52}]^{4-}$ |
| 2:5 | | $P^{5+}$ | $[P_2Mo_5O_{23}]^{6-}$ |

In the case of conversion of alkylene oxide to monoalkanolamine, suitable heteropoly acid catalysts may contain polyatoms selected from the group molybdenum, tungsten, niobium and vanadium, while the heteroatoms may be phosphorus, silicon, germanium, and arsenic. Preferably the heteroatoms are phosphorus or silicon. These heteropoly acids would likely have the Keggin structure, $H_{8-n}[XM_{12}O_{40}]$, where X=P or Si, M=Mo or W and n is an integer which is 4 or 5.

The preferred heteropoly acids for the practice of this invention include 12-molybdophosphoric acid, $H_3PMo_{12}O_{40}$, 12-tungstophosphoric acid, molybdosilicic acid, $H_4SiMo_{12}O_{40}$ and 12-tungstosilicic acid. Said acids are generally used as their hydrates. Said montmorillonite clays may be treated with heteropoly acids by any number of techniques, but generally it is most convenient to treat the clay with a solution of heteropoly acid in water, or suitable organic solvent, using the incipient wetness technique. The modified clays are then dried and calcined. A typical experimental procedure is described in the accompanying examples.

The weight percent of heteropoly acid to montmorillonite clay should be such that the concentration of the polyatom (Mo, W, Nb or V) in the formulated catalyst is in the range of 0.1 wt % to 30 wt %, although concentrations outside this range may also be employed. Where the heteropoly acid is, for example, 12-molybdophosphoric acid, supported on montmorillonite clay, a suitable quantity of molybdenum is 1-10.0 wt %. In the preparation of a tungstophosphoric acid-on-clay catalyst, on the other hand, the tungsten content may be 0.1-10.0 wt %.

Said heteropoly acid modified montmorillonite clay catalysts perform better in the desired reaction (Eq. 1) than standard literature catalysts, such as the acidic ion-exchange resins. This improved performance is illustrated in the accompanying examples.

The performance of said montmorillonite clays in the synthesis of monoalkanolamines (Eq. 1) may also be further enchanced by modification of the structure of said acidic clays by treatment with certain Group IIIA and Group IVA derivatives.

The Group IVA derivatives that are useful in the subject reaction include Group IVA salts, oxides and complexes, but particularly their halide salts. Preferred reactants include titanium(IV) chloride, zirconium(IV) chloride and titanium(IV) bromide. The preferred Group IIIA derivatives are their salts, particularly aluminum(III) chloride.

The clays may be treated with these Group III or IVA derivatives by any number of techniques, but generally it is most convenient to treat the clay either by vapor deposition or with a solution or suspension of such Group III or IVA derivative in water, or a suitable organic solvent, using the incipient wetness technique. The modified clays are then dried and calcined. A typical experimental procedure is outlined in the accompanying examples.

The weight percent of Group III or IVA derivative to montmorillonite clay should be such that the concentration of the aluminum, titanium or zirconium in the formulated catalyst is in the range of 0.1 to 30.0 wt %, although concentrations outside this range may also be employed.

Again said Group III and IVA modified montmorillonite clays perform better as catalysts in the desired reaction (Eq. 1) than standard literature catalysts - particularly in the area of productivity. This improved performance is illustrated by the accompanying examples.

Preparation of the monoalkanolamines may be conducted in a continuous slurry bed reactor or in a fixed-bed, continuous flow reactor. For practical reasons a fixed bed process is preferred. The ethylene oxide and ammonia are generally pumped upflow into a reactor containing the acid activated clay. In all cases the catalyst concentration should be sufficient to provide the desired catalytic effect.

The reaction should be carried out under a pressure that is at least as high as the vapor pressure of ammonia at the highest temperature to which the reaction mixture is brought during the reaction to ensure that the reactants remain in the liquid phase throughout the reaction.

Production of monoalkanolamines can generally be conducted at temperatures from 50° to 300° C.; the preferred range is 80° to 250° C. The operating pressure may be from zero to 15,000 psig, or higher. The preferred pressure range is 100 to 10,000 psig.

Generally alkylene oxide, and especially ethylene oxide, conversions are quantitative in continuous unit operations. An excess of ammonia should be used. The molar ratio of ammonia to alkylene oxide should be in the range from about 10:1 to about 40:1. Using these mole ratios a yield to the monoalkanolamine of 70 to 90 mol % and higher is possible. Generally, the yield to monoalkanolamine increases as the mole ratio of ammonia to oxide is increased with 40:1 as the upper limit beyond which additional ammonia is not beneficial.

After the conclusion of the reaction, the ammonia is easily separated by reducing the pressure to below that at which the ammonia is in a gaseous phase, so that the ammonia can be separated as a gas and then recycled. The gaseous recycled ammonia is, of course, repressurized to the liquid phase before blending with more alkylene oxide. It is also possible to distill off the unreacted ammonia under pressure and recycle it as a liquid.

The pressure over the alkanolamine mixture is then released.

Typically, monoalkanolamines, such as monoethanolamines are generated continuously in up to ca. 80–90 wt % concentration in the crude product liquid effluent. Dialkanolamines and trialkanolamines, such as diethanolamine (DEA) and triethanolamine (TEA), make up the majority of the remaining products.

Yields of monoethanolamine of >70 mol % are achieved at total liquid hourly space velocities (LHSV) of 1 to 20 under the conditions described supra. LHSVs of 5–15, or greater, have been demonstrated to be particularly useful in achieving quantitative ethylene oxide conversion.

Here LHSV is defined as follows:

$$LHSV = \frac{\text{Weight Of Total Liquid Feed Run Through The Reactor Per Hour}}{\text{Volume of Catalyst In Reactor}}$$

Conversion of alkylene oxide (wt %) is estimated in the following examples using the equation:

$$\frac{\text{Weight Of (Alkylene Oxide In Feed} - \text{Alkylene Oxide Residues In Product)}}{\text{Weight of Alkylene Oxide in Feed}} \times 100$$

For an experiment in which the alkylene oxide is ethylene oxide the "weight of ethylene oxide residues in Product" ($W_R$) is estimated from:

$W_R$ = Weight of Product × [$F_1$ × (A% MEA) +

$F_2$ × (A% DEA) + $F_3$ × (A% TEA)]/100 such that $F_1$ = weight fraction of ethylene oxide residues in MEA = 0.7213

$F_2$ = weight fraction of ethylene oxide residues in DEA = 0.8381

$F_3$ = weight fraction of ethylene oxide residues in TEA = 0.8859

Selectivity to Monoethanolamine (MEA) is estimated from:

$$\frac{\text{Monethanolamine (MEA) In Product Liquid}}{\text{Total Ethanolamines (MEA + DEA + TEA) In Product}} \times 100$$

Catalyst productivity is measured in terms of:

grams MEA produced/cc of catalyst/hour

The examples which follow illustrate the generation of monoethanolamine from ethylene oxide plus ammonia using acid treated clay catalysts, particularly modified montmorillonite clay catalysts. The examples are only intended as a means of illustration and it should be understood that the invention is not meant to be limited thereby.

EXAMPLE A

This example illustrates the synthesis of a 12-tungstophosphoric acid modified montmorillonite clay.

To a 2-liter aqueous solution of 12-tungstophosphoric acid (0.01N, containing 57.6 g of $H_3PO_4 WO_3 xH_2O$) is added with stirring 200 g of extruded montmorillonite clay (Grade 62, from Harshaw/Filtrol, 1/16" extrudates). Stirring is maintained for 2 days at room temperature. The extrudates are then recovered by filtration, washed with distilled water until tungsten is no longer detected in the washings, dried in vacuo at 40° C., and sieved through #10 and 20 mesh screens.

Tungsten content of the finished extrudates is 0.3 wt %.

EXAMPLE B

This example illustrates the synthesis of a titanium chloride modified montmorillonite clay.

To a 2-liter aqueous solution of titanium(IV) chloride (190 g) is added with stirring 200 g of montmorillonite clay (Grade 62, from Harshaw/Filtrol, 1/16" extrudates). Stirring is maintained for 2 days at room temperature. The extrudates are then recovered, by filtration, washed with distilled water until titanium is no longer detected in the washings, dried in vacuo at 40° C., and sieved through #10 and 40 mesh screens.

Titanium content of the finished extrudates is 2.0 wt %.

EXAMPLES 1–4

These examples illustrate the performance of an acidic montmorillonite clay as catalyst for monoethanolamine (MEA) synthesis over a range of operating conditions.

A 100 cc stainless steel tubular reactor (0.75 mmid.) was half-filled with glass beads, atop which was placed 50 cc of an acid activated clay (Harshaw/Filtrol Grade 24 acidity 8.5 mg KOH/g, surface area 425 m²/g). The reactor was heated in an aluminum block while ammonia and ethylene oxide were pumped, upflow, through the reactor over a range of feed rates. Back pressure was maintained at 2500 psi. The product effluent was collected and analyzed by gas chromatography analysis.

The data are presented below in Table II.

It may be noted from the data that:

(a) MEA selectivity is typically in the range of 74.5→78.8%.

(b) The remainder of the product is DEA and TEA.

(c) Comparing experiments 2 and 3, doubling the total flow rate from a LHSV of ca. 7.9 to 14.8 does not lead to a loss of EO conversion, or a loss in MEA selectivity.

(d) Productivity in Example 3 is 1.77 g MEA/cc/hr, the productivity in Example 2 is 0.85 g MEA/cc/hr.

TABLE II

| EX. | CATALYST | OPERATING TEMP. (°C.) | FEED RATES EO (g/hr) | FEED RATES NH3 (g/hr) | NH3/EO MOLAR RATIO | PRODUCT (g/hr) | PRODUCT COMP. (%) MEA | PRODUCT COMP. (%) DEA | PRODUCT COMP. (%) TEA | EO CONV. (%) |
|---|---|---|---|---|---|---|---|---|---|---|
| 1 | Clay 24 | 119 | 43 | 352 | 21.2 | 56 | 76.4 | 18.4 | 4.8 | 97 |
| 2 | Clay 24 | 142 | 43 | 350 | 21.2 | 57 | 74.5 | 19.1 | 5.9 | 99 |
| 3 | Clay 24 | 140 | 87 | 651 | 19.4 | 117 | 75.7 | 20.0 | 4.0 | >99 |

TABLE II-continued

| EX. | CATALYST | OPERATING TEMP. (°C.) | ← FEED RATES → | | NH₃/EO MOLAR RATIO | PRODUCT (g/hr) | ←PRODUCT COMP. (%)→ | | | EO CONV. (%) |
|---|---|---|---|---|---|---|---|---|---|---|
| | | | EO | (g/hr) NH3 | | | MEA | DEA | TEA | |
| 4 | Clay 24 | 140 | 55 | 485 | 22.8 | 70 | 78.8 | 18.3 | 2.3 | 95 |

COMPARATIVE EXAMPLES 5-9

These five examples illustrate the comparative performance of acidic, standard, ion-exchange resins for monoethanolamine (MEA) synthesis.

Using the same 100 cc tubular reactor of Example 1, charged with glass beads and 50 cc of low ion exchange resin (AMBERLYST®-15 or AMBERLYTE® 200), the reactor was heated to temperature while ammonia and ethylene oxide were pumped, upflow, through the unit. Again the pressure was maintained at 2500 psi. In each run the product effluent was collected and analyzed by gas chromtography analysis.

The data are presented in Table III.

It may be noted that in these experiments, doubling the total flow (e.g. Examples 8 and 9, from a LHSV of ca. 7.6 to 15.9) leads to a substantial loss in EO conversion (from 100% to 75%).

The productivity in Example 9 is 1.49 g MEA/cc/hr, and in Example 8 it is 0.88 g MEA/cc/hr.

EXAMPLES 10-14

These examples illustrate the activity of two other acidic montmorillonite Clays-A Harshaw/Filtrol Grade 25 (10/20 Mesh) granular clay having a surface area of 383 m²/g and an acidity index of 12.3, and Harshaw/Filtrol Grade 62, 1/16" diameter extrudates having a surface area of 275 m²/g KOH.

Both catalysts were evaluated using the equipment, and following the procedures of Example 1. Analyses data for typical product effluents from these runs are given in Table IV.

TABLE IV

| EX. | CATALYST | OPERATING TEMP. (°C.) | ← FEED RATES → | | NH₃/EO MOLAR RATIO | PRODUCT (g/hr) | ←PRODUCT COMP. (%)→ | | | EO CONV. (%) |
|---|---|---|---|---|---|---|---|---|---|---|
| | | | EO | NH3 | | | MEA | DEA | TEA | |
| 10 | Clay 62 | 140 | 45 | 349 | 20.1 | 55 | 75.6 | 18.5 | 5.4 | 92.1 |
| 11 | Clay-25 | 140 | 43 | 340 | 20.5 | 57 | 72.3 | 22.3 | 5.2 | 100 |
| 12 | Clay-25 | 130 | 43 | 340 | 20.5 | 54 | 75.2 | 20.0 | 4.5 | 93.5 |
| 13 | Clay-25 | 120 | 46 | 340 | 21.9 | 51 | 76.6 | 19.4 | 3.9 | 83.0 |
| 14 | Clay-25 | 110 | 44 | 340 | 21.0 | 43 | 76.1 | 19.8 | 3.9 | 73.9 |

It may be noted that in Example 11, the Clay-25 catalyst gives quantitative ethylene oxide conversion at a LHSV of Ca. 7.7, and that in this example the MEA selectivity remains at 72.3%.

In Example 10, the productivity for Clay-62 is 0.83 g MEA/cc/hr, Example 11, Clay-25 productivity is 0.82 g MEA/cc/hr.

EXAMPLES 15-23

These examples illustrate the performance of the 12-tungstophosphoric acid modified montmorillonite clay prepared by the procedure of Example A.

The catalyst (50 cc) was charged to the reactor of Example 1 and heated under a flow of ammonia plus ethylene oxide over a range of:

(a) Ethylene oxide and ammonia feed ratios.
(b) Ethylene oxide/ammonia feed ratios.
(c) Operating temperatures and pressures.
(d) Different catalyst loadings, i.e. with either the catalyst set above the class beds as in Example 1, or distributed with the glass beds throughout the reactor.

Data for each of these runs are given in Table V.

It may be noted that:

In Example 25, where the LHSV is 4.5, the monoethanolamine selectivity is 91.8%.

In Example 22, where the LHSV is again 4.5, the ethylene oxide conversion is 98.5%.

In Example 32, where the LHSV is 18.0, productivity is 1.0 g MEA/cc/hr.

TABLE III

| EX. | CATALYST | OPERATING TEMP. (°C.) | ← FEED RATES → | | NH₃/EO MOLAR RATIO | PRODUCT (g/hr) | ←PRODUCT COMP. (%)→ | | | EO CONV. (%) |
|---|---|---|---|---|---|---|---|---|---|---|
| | | | EO | (g/hr) NH3 | | | MEA | DEA | TEA | |
| 5 | AMBERLYST® | 125 | 44 | 337 | 19.8 | 58 | 83.4 | 15.5 | 1.0 | 98 |
| 6 | 15 | 100 | 88 | 690 | 20.3 | 70 | 77.4 | 20.3 | 2.1 | 59 |
| 7 | AMBERLYTE® | 140 | 43 | 336 | 20.2 | 57 | 78.2 | 19.6 | 2.0 | 99 |
| 8 | 200 | 139 | 41 | 337 | 20.9 | 55 | 80.3 | 17.7 | 2.0 | 100 |
| 9 | " | 138 | 90 | 703 | 20.2 | 94 | 79.2 | 18.6 | 2.1 | 75 |

TABLE V

| Ex. | OPERATING TEMP (°C.) | OPERATING PRESSURE (psi) | FEED RATE (g/hr) EO | (g/hr) NH₃ | CATALYST BED | PRODUCT (g/hr) | ←PRODUCT COMPOSITION→ | | | EO CONV (%) |
|---|---|---|---|---|---|---|---|---|---|---|
| | | | | | | | MEA | DEA | TEA | |
| 15 | 110 | 2500 | 45.4 | 350 | a | 40 | 75.2 | 19.1 | 5.6 | 68.5 |

TABLE V-continued

| Ex. | OPERATING TEMP (°C.) | OPERATING PRESSURE (psi) | FEED RATE (g/hr) EO | FEED RATE (g/hr) NH₃ | CATALYST BED | PRODUCT (g/hr) | PRODUCT COMPOSITION MEA | PRODUCT COMPOSITION DEA | PRODUCT COMPOSITION TEA | EO CONV (%) |
|---|---|---|---|---|---|---|---|---|---|---|
| 16 | 120 | 2500 | 45.4 | 350 | a | 39 | 76.4 | 18.5 | 4.7 | 65.2 |
| 17 | 130 | 2500 | 45.4 | 350 | a | 49 | 75.2 | 19.2 | 5.3 | 82.2 |
| 18 | 110 | 3000 | 82.5 | 817 | a | 25 | 55.5 | 34.5 | 8.9 | 24.1 |
| 19 | 150 | 3000 | 7.5 | 218 | a | 8 | 86.1 | 10.7 | 3.0 | 81.1 |
| 20 | 130 | 2250 | 27.0 | 540 | a | 25 | 85.8 | 12.1 | 1.9 | 62.8 |
| 21 | 110 | 1500 | 82.5 | 817 | a | 24 | 52.7 | 35.7 | 11.5 | 22.2 |
| 22 | 150 | 1500 | 20.6 | 204 | a | 27 | 39.6 | 30.8 | 29.1 | 98.5 |
| 23 | 130 | 2250 | 27.0 | 540 | a | 24 | 83.3 | 14.5 | 2.2 | 61.6 |
| 24 | 150 | 1500 | 29.3 | 863 | a | 20 | 82.2 | 14.9 | 2.8 | 49.5 |
| 25 | 110 | 3000 | 7.5 | 218 | a | 6 | 91.8 | 5.0 | 0.7 | 68.7 |
| 26 | 110 | 1500 | 20.6 | 204 | b | 18 | 80.8 | 14.9 | 2.5 | 63.9 |
| 27 | 110 | 1500 | 7.5 | 218 | b | 5 | 91.0 | 7.4 | 0.8 | 47.7 |
| 28 | 130 | 2250 | 27.0 | 540 | b | 17 | 87.1 | 10.6 | 1.3 | 48.1 |
| 29 | 110 | 3000 | 29.3 | 863 | b | 7 | 59.9 | 32.7 | 7.0 | 19.6 |
| 30 | 150 | 3000 | 20.6 | 204 | b | 16 | 82.5 | 14.3 | 2.7 | 92.6 |
| 31 | 130 | 2250 | 27.0 | 540 | b | 17 | 86.2 | 12.1 | 1.1 | 44.5 |
| 32 | 150 | 3000 | 82.5 | 817 | b | 67 | 75.7 | 20.3 | 3.8 | 61.3 |
| 33 | 150 | 1500 | 29.3 | 863 | b | 15 | 81.6 | 16.0 | 1.8 | 38.2 | a Catalyst of Example A distributed throughout the reactor
b Catalyst of Example A at top half of the reactor

EXAMPLES 34–45

These examples illustrate the performance of the titania modified montmorillonite clay prepared by the procedure of Example B.

The catalyst (50 cc) was charged to the reactor of Example 1 and heated under a flow of ammonia plus ethylene oxide over a range of:
(a) Ethylene oxide and ammonia feed rates.
(b) Ethylene oxide/ammonia feed ratios.
(c) Operating temperatures.
The operating pressure was set at 2500 psi.
Data for each of these runs are given in Table VI.
It may be noted that:

In Examples 37 and 38, where the LHSV's are Ca. 7.9, the ethylene oxide conversion level is >98%.

In Example 39, where the LHSV is also 7.9, the monoethanolamine selectivity is 74.9%.

In Example 42, where the LHSV is 15.3, the productivity is 1.6 g MEA/cc/hr.

TABLE VI

| EX. | OPERATING TEMP (°C.) | FEED RATES (g/hr) EO | FEED RATES (g/hr) NH₃ | Product (g/hr) | PRODUCT COMPOSITION % MEA | DEA | TEA | EO CONV (%) |
|---|---|---|---|---|---|---|---|---|
| 34 | 100 | 44 | 349 | 28 | 70.9 | 22.0 | 7.0 | 48.6 |
| 35 | 120 | 44 | 349 | 43 | 72.9 | 20.6 | 5.9 | 73.5 |
| 36 | 140 | 46 | 349 | 57 | 69.4 | 22.3 | 7.2 | 92.5 |
| 37 | 160 | 46 | 349 | 60 | 58.5 | 26.9 | 13.3 | 98.9 |
| 38 | 180 | 45 | 349 | 58 | 45.4 | 27.4 | 26.7 | >99 |
| 39 | 120 | 45 | 349 | 50 | 74.9 | 20.2 | 4.8 | 83.4 |
| 40 | 120 | 89 | 671 | 48 | 68.3 | 25.6 | 5.9 | 40.8 |
| 41 | 140 | 90 | 671 | 86 | 72.7 | 21.9 | 5.3 | 72.1 |
| 42 | 161 | 92 | 671 | 115 | 68.7 | 22.3 | 8.8 | 94.8 |
| 43 | 120 | 48 | 231 | 55 | 68.8 | 22.7 | 8.3 | 86.8 |
| 44 | 140 | 45 | 231 | 59 | 64.4 | 25.4 | 10.1 | 99.7 |
| 45 | 159 | 46 | 231 | 58 | 56.1 | 27.8 | 16.0 | 97.6 |

EXAMPLES 46–55

These examples illustrate the performance of an acidic clay, Harshaw/Filtrol Grade 113 powdered clay, sieved to remove material finer than a mesh of 200 prior to use. This clay has a surface area of 300 m²/g and an acidity of 10 mg KOH/gm. It was evaluated using the equipment, and following the procedures of Example 1. Analyses data for typical product effluents from these runs are given in Table VII.

It may be noted that:

In Example 52, where the LHSV is 7.9, NH₃/EO Ratio is 3.9, productivity is 1.6 g MEA/cc/hr.

In Example 54, where the LHSV is 15.3, NH₃/EO Ratio is 7.8, productivity is 1.5 g MEA/cc/hr.

TABLE VII

| EX. | OPERATING TEMP (°C.) | FEED RATES (g/hr) EO | FEED RATES (g/hr) NH₃ | Product (g/hr) | PRODUCT COMPOSITION % MEA | DEA | TEA | EO CONV (%) |
|---|---|---|---|---|---|---|---|---|
| 46 | 110 | 48 | 349 | 16 | 84.1 | 13.4 | 2.6 | 23.9 |
| 47 | 118 | 44 | 349 | 57 | 79.2 | 17.8 | 2.9 | 97.4 |
| 48 | 132 | 45 | 349 | 59 | 79.0 | 17.7 | 3.2 | 97.2 |
| 49 | 144 | 44 | 349 | 57 | 77.7 | 18.7 | 3.6 | 96.1 |
| 50 | 123 | 43 | 349 | 59 | 77.1 | 19.7 | 3.1 | >99 |
| 51 | 127 | 30 | 363 | 42 | 85.6 | 13.1 | 1.2 | >99 |
| 52 | 120 | 81 | 313 | 111 | 70.3 | 24.7 | 4.8 | >99 |

TABLE VII-continued

| EX. | OPERATING TEMP (°C.) | FEED RATES (g/hr) EO | (g/hr) NH₃ | Product (g/hr) | PRODUCT COMPOSITION % MEA | DEA | TEA | EO CONV (%) |
| --- | --- | --- | --- | --- | --- | --- | --- | --- |
| 53 | 125 | 45 | 349 | 63 | 80.2 | 17.4 | 2.2 | >99 |
| 54 | 125 | 87 | 680 | 97 | 76.7 | 18.3 | 2.5 | 80.9 |
| 55 | 120 | 25 | 177 | 34 | 79.6 | 17.6 | 2.6 | >99 |

EXAMPLE 56

Following the procedure of Examples 11 to 14, the Clay-25 catalyst was tested under the following conditions.
125° C. operating temperature.
91 g/hr EO feed rate.
658 g/hr NH₃ feed rate.
Analysis of the product effluent shows:
MEA selectivity of 73.0%
MEA productivity of 1.2 g/cc/hr.

What is claimed is:

1. A process for preparing monoalkanolamines which comprises reacting an alkylene oxide with an excess of ammonia in the presence of an acid treated clay catalyst comprising an acidic montmorillonite clay treated with a heteropoly acid selected from the group consisting of 12-tungstophosphoric acid, 12-tungstosilicic acid, 12-molybdophosphoric acid and 12-molybdosilicic acid, said monoalkanolamine being prepared at an operating temperature in the range of 50° to 300° C. and an operating pressure of 0 to 15,000 psi or greater.

2. A process for preparing monoalkanolines which comprises reacting an alkylene oxide with an excess of ammonia in the presence of an acid-treated clay catalyst comprising an acidic montmorillonite clay treated with a Group III or IVA halide, said monoalkanolamine being prepared at an operating temperature in the range of 50° to 300° C. and a pressure of 0 to 15,000 psi.

3. The process of claim 1 wherein the monoalkanolamines and the alkylene oxides have from 2 to 4 carbon atoms.

4. The process of claim 3 wherein the monoalkanolamine is monoethanolamine and the alkylene oxide is ethylene oxide.

5. The process of claim 1 wherein the molar ratio of ammonia to alkylene oxide is within the range of from about 10:1 to about 40:1.

6. The process of claim 1 wherein the pressure ranges from about 500 psig to 10,000 psig.

7. The process of claim 1 wherein the temperature ranges from 80° C.–250° C.

8. The process of claim 1 wherein the acid treated montmorillonite clays have a surface area of 200 to 1000 m²/g.

9. The process of claim 1 wherein the heteropoly acid treated montmorillonite clay has a tungsten or molybdenum content in the range of 0.1 to 30 wt %.

10. The process of claim 3 wherein the Group III or Group IVA halide is selected from the group consisting of titanium(IV) chloride, zirconium(IV) chloride and aluminum chloride.

11. The process of claim 10 wherein the Group III or IVA treated montmorillonite clay has a titanium, zirconium or aluminum content in the range of 0.1 to 30 wt %.

12. The process of claim 1 wherein the process is conducted continuously and in the liquid phase.

13. A process for preparing monoethanolamine which comprises reacting ethylene oxide with an excess of ammonia in the presence of a tungstophosphoric acid modified montmorillonite clay catalyst having a surface area of 200–1000 m²/g at a temperature of 80° C. to 250° C. and a pressure of 500 psig to 10,000 psig.

* * * * *